US008303790B2

(12) United States Patent
McNeill et al.

(10) Patent No.: US 8,303,790 B2
(45) Date of Patent: Nov. 6, 2012

(54) PRE-STAINING PROTOCOL FOR A PROTEIN SAMPLE WITH A PYRYLIUM DYE AND RESPECTIVE KIT

(75) Inventors: Helen McNeill, Edinburgh (GB); Kenneth G. Macnamara, Edinburgh (GB)

(73) Assignee: Agilent Technologies, Inc., Loveland, CO (US)

( * ) Notice: Subject to any disclaimer, the term of this patent is extended or adjusted under 35 U.S.C. 154(b) by 112 days.

(21) Appl. No.: 12/678,097

(22) PCT Filed: Sep. 12, 2008

(86) PCT No.: PCT/GB2008/003092
§ 371 (c)(1),
(2), (4) Date: Mar. 23, 2010

(87) PCT Pub. No.: WO2009/034334
PCT Pub. Date: Mar. 19, 2009

(65) Prior Publication Data
US 2010/0300881 A1    Dec. 2, 2010

(30) Foreign Application Priority Data
Sep. 14, 2007 (GB) .................................. 0718012.8

(51) Int. Cl.
*G01N 27/447* (2006.01)
*G01N 27/453* (2006.01)
(52) U.S. Cl. ........................................ 204/461; 204/606
(58) Field of Classification Search .......... 204/456–470, 204/606–621
See application file for complete search history.

(56) References Cited

U.S. PATENT DOCUMENTS

| 6,703,484 | B2 * | 3/2004 | Chatterjee et al. | 530/350 |
| 2001/0027921 | A1 * | 10/2001 | Chan et al. | 204/469 |
| 2005/0079104 | A1 * | 4/2005 | Polwart et al. | 422/100 |
| 2009/0294288 | A1 * | 12/2009 | May et al. | 204/461 |

FOREIGN PATENT DOCUMENTS
GB    2436048    2/2009

OTHER PUBLICATIONS

B. K. Hofelschweiger, Doctoral Dissertation, "The Pyrylium Dyes: A New Class of Biolabels. Synthesis, Spectroscopy, and Application as Labels and in General Protein Assay", University of Regensburg, Jun. 2005.*
R. J. Meier, et al., "SDS-Page of Proteins Using a Chameleon-Type of Fluorescent Prestain", Analytical Chemistry, vol. 80, No. 15, Aug. 15, 2008, p. 6274-6279.*
Craig et al., "Determination of picomolar concentrations of proteins using novel amino reactive chameleon labels and capillary electrophoresis laser-induced fluorescence detection," *Electrophoresis*, vol. 26, 2005, pp. 2208-2213.
Hoefelschweiger et al., "Novel type of general protein assay using a chromogenic and fluorogenic amine-reactive probe," *Analytical Biochemistry*, vol. 344, 2005, pp. 122-129.
Wetzl et al., "Chameleon Labels for Staining and Quantifying Proteins," *Angew. Chem. INt. Ed.*, vol. 43, 2004, pp. 5400-5402.

* cited by examiner

*Primary Examiner* — J. Christopher Ball

(57) ABSTRACT

The invention relates to a protocol for pre-staining a protein prior to electrophoresis, an electrophoresis method including the protocol, and a kit for carrying out the protocol. The protocol comprises the steps of incubating the protein sample with a pyrylium dye in the presence of a buffer, a detergent and a denaturing agent.

20 Claims, 21 Drawing Sheets pH  8.0   8.5   9.0   9.3   10   10.5

CAPSO  CHES  HEPES  TB  Phos  AM1  AM2  Tris

PRE-STAINING PROTOCOL FOR A PROTEIN SAMPLE WITH A PYRYLIUM DYE AND RESPECTIVE KIT

This invention relates to a protocol for pre-staining a protein prior to electrophoresis, an electrophoresis method including the protocol, and a kit for carrying out the protocol.

Pyrylium dyes are heterocyclic aromatic compounds with a covalently bonded chromophore, which react with primary amines under mild conditions in buffered solutions and organic solvents, to form stable pyridinium analogues. On conjugation to a primary amine the chromophore undergoes a shift in absorbance maximum, a decrease in molar extinction coefficient and an increase in emission intensity to give a greater quantum yield in comparison to the unconjugated dye.

Pyrylium dyes have the following general structure:

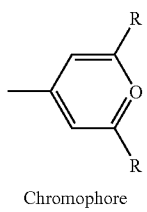

Chromophore

Two dyes in particular are currently commercially available and are sold in kit form with other reagents, consisting of either CE Dye 503 or CE Dye 540 and a relevant buffer (Active Motif Inc.). In the literature which supports these reagents [Craig et al., Electrophoresis 26, 2208-2213], CE Dye 503 is referred to as Py-1 and CE Dye 540 as Py-6.

The structures of some dyes are as follows:

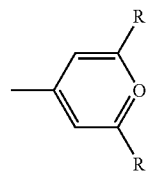

Py-1

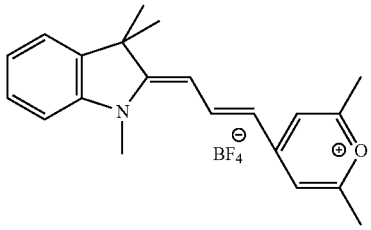

Py-2

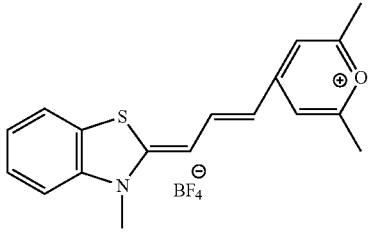

Py-4

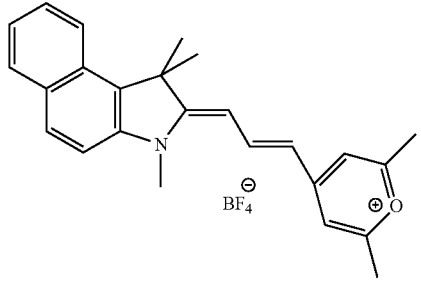

Py-6

Pyrylium

Pyrylium dyes interact with amines on proteins (or amino-modified DNA) to form compound analogues. The dyes specifically interact with lysine residues; an abundant, surface localised amino acid present in almost equal percentages in proteins.

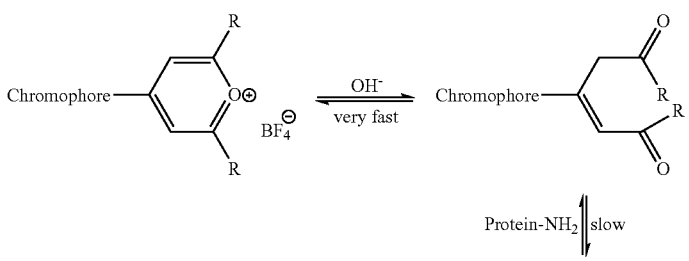

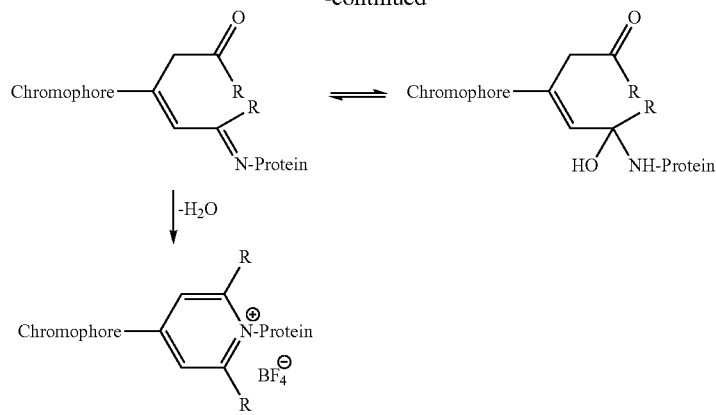

A large group of pyrylium dyes have been investigated. Of these, it has been found that there are a number that do not bind effectively to proteins because they are sterically hindered at the reactive site (the oxygen on the pyrylium ring). The sterically hindered dyes do not readily bind covalently to the protein and therefore have only a week interaction giving an unstable protein-dye conjugate.

A discussion of the use of pyrylium dyes for the determination of picomolar concentrations of proteins by capillary electrophoresis laser-induced fluorescence detection methods can be found in the Craig et al reference supra. This reference discloses protocols for the pre-staining of protein samples with Py-1 or Py-6 before capillary electrophoresis. In reference Wetzl et al., [Angew. Chem. Int. Ed. 2004. 43, 5400-5402], it is disclosed that Py-1, Py-3 and Py-5 can be used as protein labels post gel electrophoresis. It is known from the prior art that varying the basic conditions of incubation such as dye concentration, temperature, time and buffer can influence the effectiveness of the labelling process, and that for a given dye there is a basic set of conditions that work best.

Staining proteins is usually carried out following gel electrophoresis and can be a time consuming procedure. The advantage of these compounds in comparison to other protein stains is that they are small, impart virtually no change in protein size or charge following binding and therefore have a minimal effect on the electrophoretic movement of the protein molecule. It would be advantageous therefore to be able to use them as a pre-stain protocol prior to gel electrophoresis. However, it has been found that the pre-staining techniques described in the prior art do not provide acceptable results, either for prestaining samples to be run on slab gels, or for prestaining samples to be run on small scale automated gel systems. It is an object of the invention to seek to mitigate problems such as this.

According to the invention there is provided a protocol for pre-staining a protein sample prior to electrophoresis, comprising the steps of incubating the protein sample with a pyrylium dye in the presence of a buffer, a detergent and a denaturing agent. It has been found that incubating using this combination of constituents enhances the ability of pyrylium dyes to stain both low and high molecular weight proteins with improved linearity and high intensity.

It is preferred that the pyrylium dye is a non-sterically hindered dye. It is preferred that pyrylium dye when unconjugated has a low quantum yield, and when conjugated, a high quantum yield. It is preferred that the detergent comprises SDS. The denaturing agent may comprise one or more of DTT, tributyl-phosphine (TBP), tris(2-carboxyethyl)phosphine (TCEP).

It is preferred that incubation is carried out at a pH from 9 to 10. Below pH 9 labelling is less efficient, whilst at pH 10.5 sample staining is reduced and protein bands are broader such that resolution is compromised. It is particularly preferred that incubation be carried out at about pH 9.3.

It is further preferred that incubation is carried out at a temperature of from 70 to 95° C. and for from 5 to 60 minutes, preferably at 75° C. for 7 minutes.

It is preferred that the buffer includes a sulphonate group. It has been found that such buffers also contribute to an improvement in staining both low and high molecular weight proteins with respect to linearity and intensity of stain. The buffer may comprise one or more from CAPSO, CHES, TAPS, TES and HEPES.

According to a second aspect of the invention there is provided a gel-electrophoresis method, the method comprising the steps of pre-staining a protein sample using a protocol as set out hereinabove, and electrophoresing the sample on a gel.

It is preferred that the gel is a cross-linked polyacrylamide gel.

According to a third aspect of the invention there is provided a kit for performing a protein pre-stain protocol, the kit comprising a pyrylium dye, a buffer, a detergent and a denaturing agent.

The detergent may comprise SDS. The denaturing agent may comprise one or more of DTT, tributyl-phosphine (TBP), and tris(2-carboxyethyl)phosphine (TCEP).

The buffer is preferably a buffer that includes a sulphonate group. The buffer may comprise one or more from CAPSO, CHES, TAPS, TES and HEPES.

The kit may further comprise an electrophoresis vessel, the vessel including a prepackaged electrophoresis gel. The electrophoresis vessel may preferably be an integrally formed plastics strip or continuous tape, having one or a plurality of electrophoresis volumes formed therein, each volume including a prepackaged electrophoresis gel.

The invention will further be described and illustrated by way of the following experiments and Figures.

Figure 1:
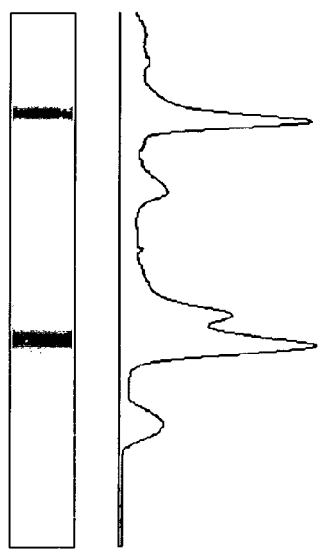
FIG. 1 shows results from a pre-stain reaction using Py-6 with samples incubated for 60 minutes at 50° C. in the presence of AM2.

1. Methods:

A series of experiments was performed to assess the efficiency of known staining protocols utilising pyrylium dyes as pre-stains for protein samples for gel-electrophoresis. The only available pre-stain protocol was that described for use before capillary electrophoresis. A pre-stain protocol was used in Höfelschweiger (PhD dissertation, University of Regensburg). In this work, Py-6, Py-1, Py-4, and Py-2 were dissolved in 100 µl DMF (to give concentrations of around 5 mM). An aliquot of 1 µl dye was added to a protein ladder in 10 µl, in bicarbonate buffer pH9. Dye was present at either 500 µM or 50 µM final concentration. Staining was performed for 30 minutes, although no temperature was given. This is the only published protocol for staining a sample prior to slab gel electrophoresis. A post gel electrophoresis staining protocol is available (Wetzl et al., (2004) Angew. Chem. Int. Ed. 43, 5400-5402).

Gels

Gels were made using acrylamide and bis-acrylamide.

Sample Preparation

A protein ladder was made using six recombinant proteins (electrophoresis grade), obtained from Sigma Aldrich, Poole, UK). Ladders were prepared with each protein present in equal amounts (2 mg/ml). Py-1, Py-2, Py-4, Py-6, and Py-8 were obtained from Active Motif Chromeon, Germany. Py-1, and Py-6 were reconstituted in DMF to give a 2.5 mM stock. Py-4 was reconstituted in DMSO to give a 26 mM stock, and Py-8 a 4 mM stock. The stock concentration of Py-2 was unknown.

Prior Art Protocol

The available pre-stain prior art protocol was the Active Motif Chromeon protocol for labelling proteins (see www.activemotif.com). This is referred to as the "manufacturers protocol" herein below. In a 48 µl reaction volume, between 1-20 µl sample was added and made up to 46 µl with either buffer AM1 or AM2. Craig et al. suggest that Buffer AM1 comprises 10 mM sodium hydrogen carbonate and buffer AM2 comprises 2.5 mM sodium tetraborate. 2 µl of dye stock were added, the contents were mixed thoroughly and incubated at room temperature for 30 minutes with AM1 buffer with Py-1, and 50° C. for 60 minutes with AM2 buffer and Py-6. This was directly scaled down to a 10 µl volume, containing 4 µl protein sample ladder, 0.25 µl pyrylium dye from stock, and 4.1 µl AM1 or AM2. The volume of ladder, dye and AM1 or AM2 buffer was always constant, and volumes made up with water when additives were used.

Modified Protocol

A modified protocol was devised as follows: 4 µl protein ladder mixture, 50 mM CHES buffer (final concentration), in the presence or absence of additives with 0.25 µl of Py-6 which had been pre diluted 1:7.5 in DMF. This gives a final concentration of Py-6 and Py-1 in a protein pre stain reaction of 8.25 µM, as opposed to the manufacturer's protocol using 62.5 µM. Reaction volumes were made to 10 µl with water, and staining was carried out using a PCR machine (TECHNE TC-512) at the required temperature. Py-8 was used at a final concentration of 100 µM.

Electrophoresis

1. Microfluidic Electrophoresis Device

Following staining, samples were denatured in loading buffer containing 20% glycerol, 0.78M sucrose, 50 mM Tris base pH8, 350 mM mercaptoethanol, and 2% SDS for 5 minutes at 95° C. A volume of 0.4 µl of sample was loaded onto a ScreenTape gel electrophoresis device. Samples were subjected to electrophoresis for 5 minutes, and images captured using the Lab901 Tape Station. Details of these of the ScreenTape® gel electrophoresis device are contained in WO03045557, WO03046542, and details of the Lab901 Tape Station can be found in WO2006085071.

2. Conventional Slab Gel

For slab gel analysis of pre stained samples, a full 10 μl reaction volume as described above was denatured with loading buffer and the entire 20 μl volume (with 1.7 μg of protein in each band) was loaded onto a NuPage 4-12% Bis-Tris HCl gel (Invitrogen). Samples were subjected to electrophoresis in the Invitrogen MES-SDS running buffer at 200V for 35 minutes, and gels were imaged using UV. To demonstrate the composition of the ladder sample and to compare with the pre staining protocol, identical gels were used to analyse the sample ladder by post staining the gels with colloidal coomassie. Following electrophoresis under the same conditions as described, gels were fixed in 40% methanol and 10% acetic acid, and post stained with colloidal coomasie blue R-250 (BioRad).

EXAMPLE 1

The experiments that make up this example were conducted in order to demonstrate the effects of detergent and denaturing additives.

Experiment 1

A pre-stain reaction was performed as set out above according to the manufacturer's protocol using Py-6. Samples were incubated for 60 minutes at 50° C. in the presence of buffer AM2, in accordance with the manufacturer's instructions.

FIG. 1 shows the result. Of the six protein bands expected, some are seen weakly, and some not at all.

Experiment 2

Experiment 1 was repeated, however this time, additives in the form of a denaturing agent and a detergent were included in the incubation mix.

Figure 6:
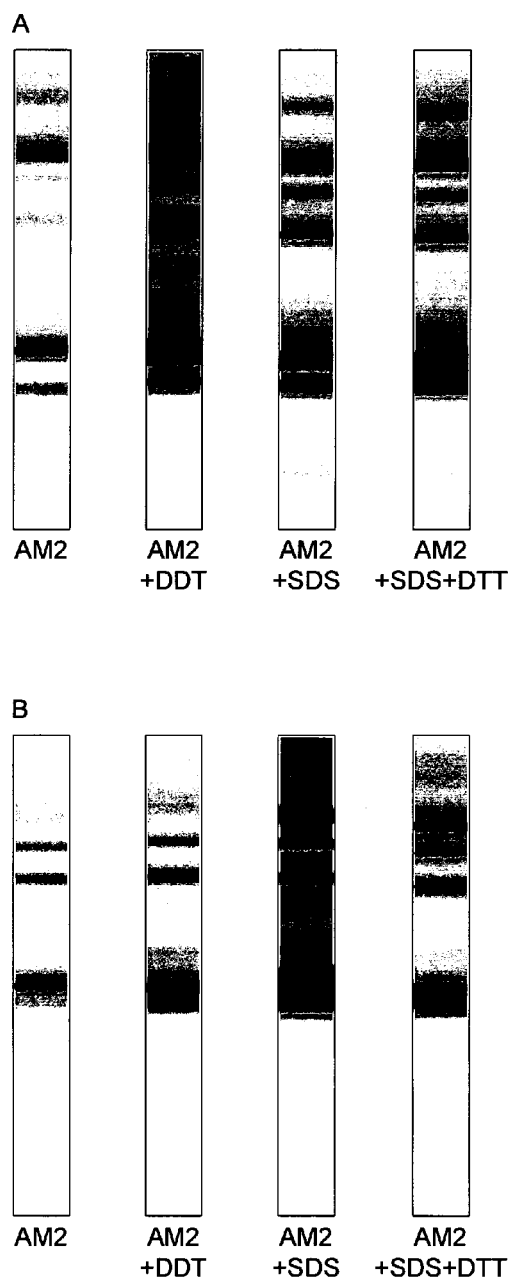
FIG. 6 shows results from a pre-stain reaction using Py-6 with samples incubated for 60 minutes at 50° C. in the presence of AM2 and with additives in form of a denaturing agent and a detergent.

FIG. 6 shows the result. Part A demonstrates the influence of DTT alone, SDS alone, and DTT with SDS, with all reactions at 50° C. for 60 minutes. With either SDS or DTT alone, labelling is improved in comparison to the AM2 sample alone, in which some protein bands are very weakly stained. DTT bands are less equally labelled. The same is true for SDS, however only when both are combined is more equal labelling observed across all proteins present in the ladder sample.

As an extension of this experiment, the temperature of incubation was increased to 95° C. and the time was decreased to 5 minutes. The result is shown in part B, where samples incubated at 95° C. for 5 minutes also show best labelling when both SDS and DTT are present.

Experiment 3

Figure 16:
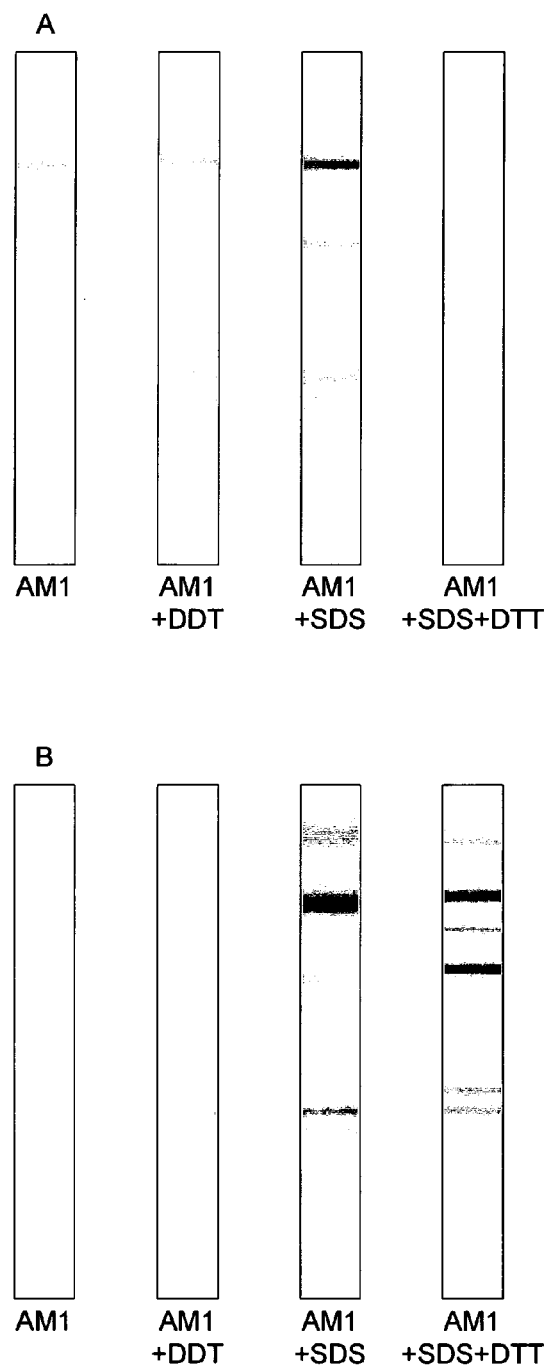
FIG. 16 shows results of test of the effect of detergent and denaturing additives when used with Py-1.
Figure 16:
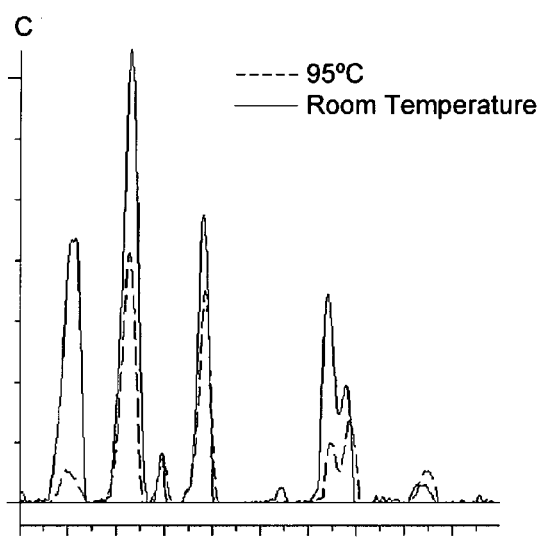

This experiment was designed to test the effect of detergent and denaturing additives when used with Py-1. The results are shown in FIG. 16. In part A, buffer AM1 at room temperature for 30 minutes stains with best linearity in the presence of additives SDS and DTT. Good labelling is also achieved in the presence of AM1 and SDS, however staining is not as linear.

In part B, the effect of increasing the temperature and reducing the incubation time was tested. AM1 buffer at 95° C. has best results in the presence of both SDS and DTT. Part C shows the electropherogram comparison between room temperature and 95° C. samples in the presence of both SDS and DTT. The increased temperature is shown to be beneficial.

Experiment 4

Figure 13:
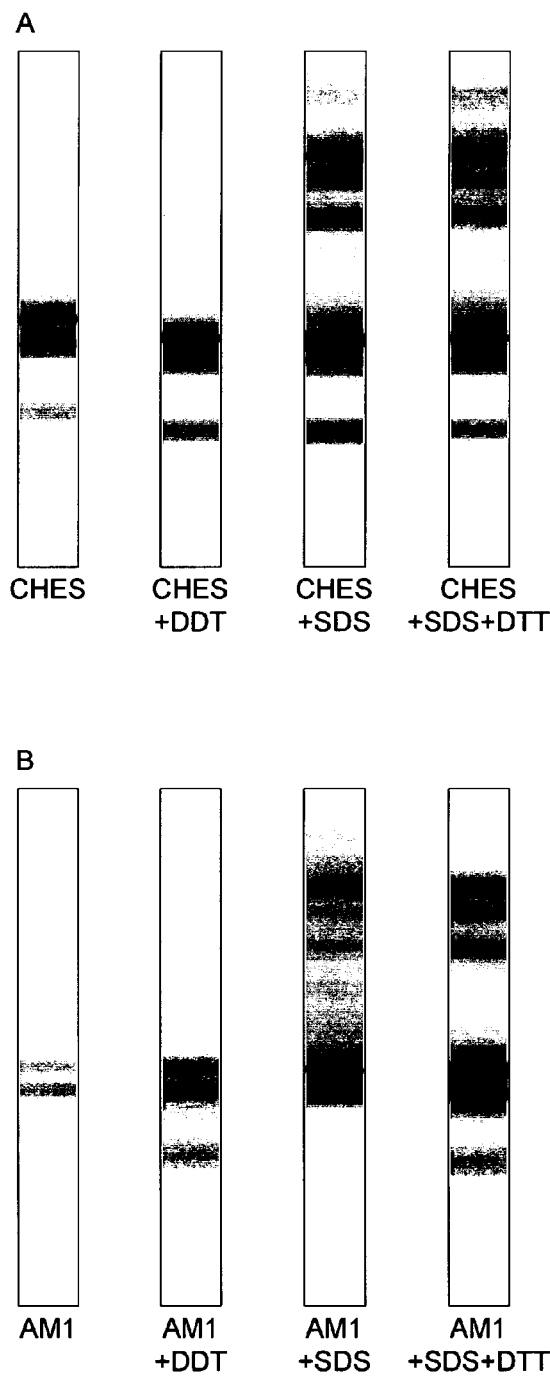
FIG. 13 shows results of the effects of denaturing and detergent additives on dye Py-4.
Figure 13:
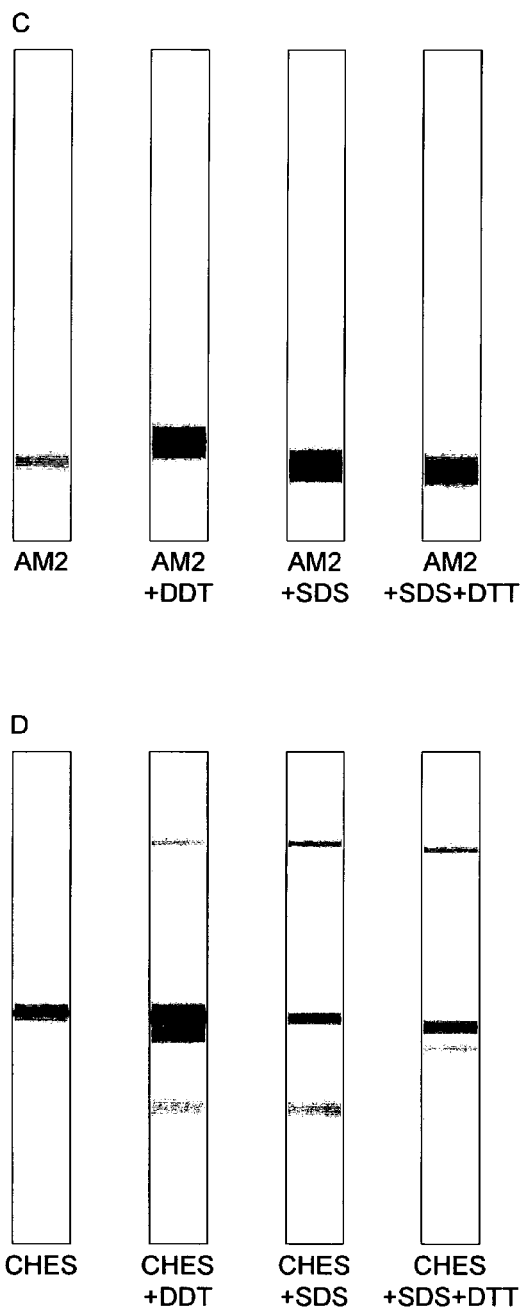

In this experiment, the effects of denaturing and detergent additives on dye Py-4 were tested. The results are shown in FIG. 13. In part A, CHES buffer with SDS or SDS with DTT successfully labelled a protein ladder after 5 minutes at 95° C. In part B, Py-4 labelling works with AM1 buffer when incubated at 95° C. for 5 minutes. In part C, Py-4 in the presence of AM2 buffer with reaction at 95° C. for 5 minutes, very poor or no protein labelling was achieved. In part D, Py-4 labelling with CHES buffer at 50° C. for 60 minutes was achieved, but again required the presence of SDS with DTT for best results.

Experiment 5

Figure 7:
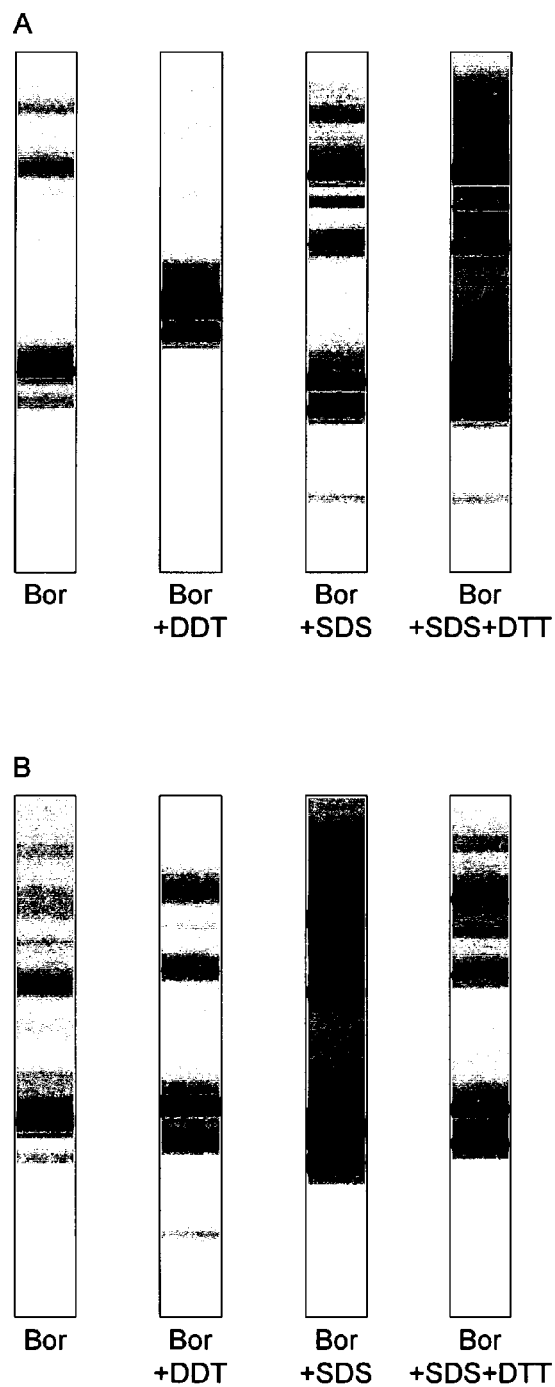
FIG. 7 shows results of a series of tests on the effect of varying the buffer.

A series of experiments was performed to test the effect of varying the buffer. FIG. 7 shows the effect of additives on pre staining with Py-6 in the presence of tetraborate buffer for 60 minutes at 50° C. In part A, the absence of additives, with 5 mM tetraborate buffer only, proteins in the ladder sample are poorly labelled. Only in the presence of SDS with DTT is labelling more uniform across all proteins and all six ladder proteins are stained. In part B, incubation of ladder sample for 5 minutes at 95° C. again shows best labelling with both SDS and DTT present for all 6 proteins labelled (SDS alone has higher background and bands are broader).

Figure 8:
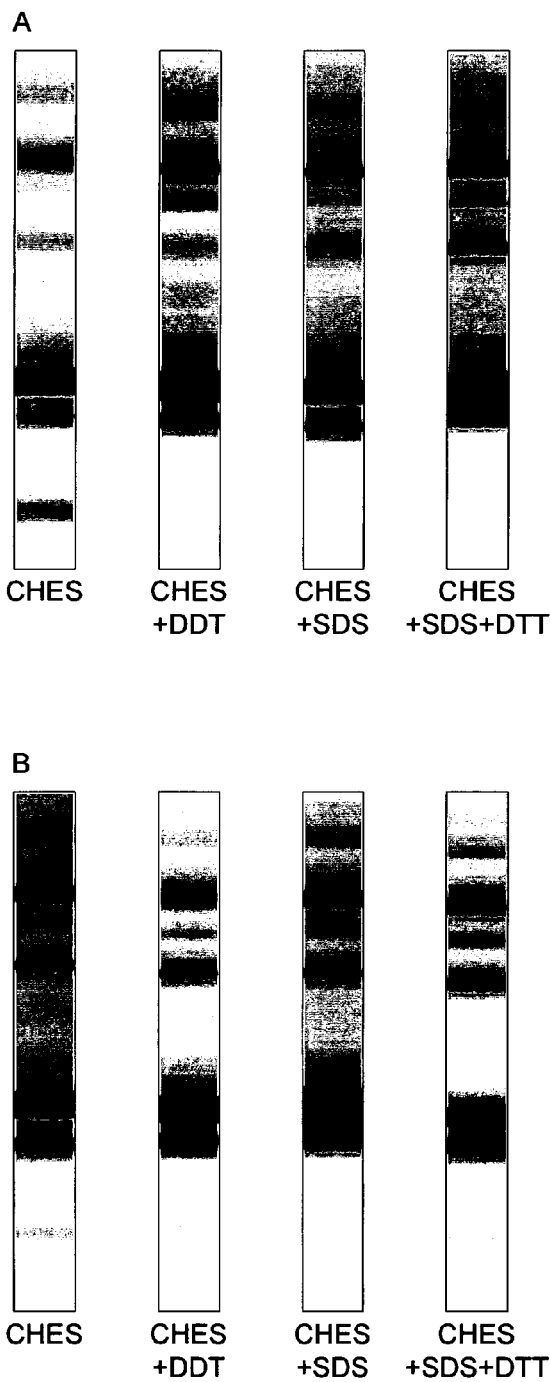
FIG. 8 shows results of the effect of sample incubation with CHES buffer.

FIG. 8 shows the effect of sample incubation with CHES buffer. In part A, at 50° C. only the presence of SDS and DTT together improve staining of all six proteins, and give more equal labelling intensity. With CHES alone, or CHES with DTT some bands are very poorly stained, or absent. In part B, samples with CHES buffer incubated at 95° C. for 5 minutes again were best labelled with both SDS and DTT.

Figure 11:
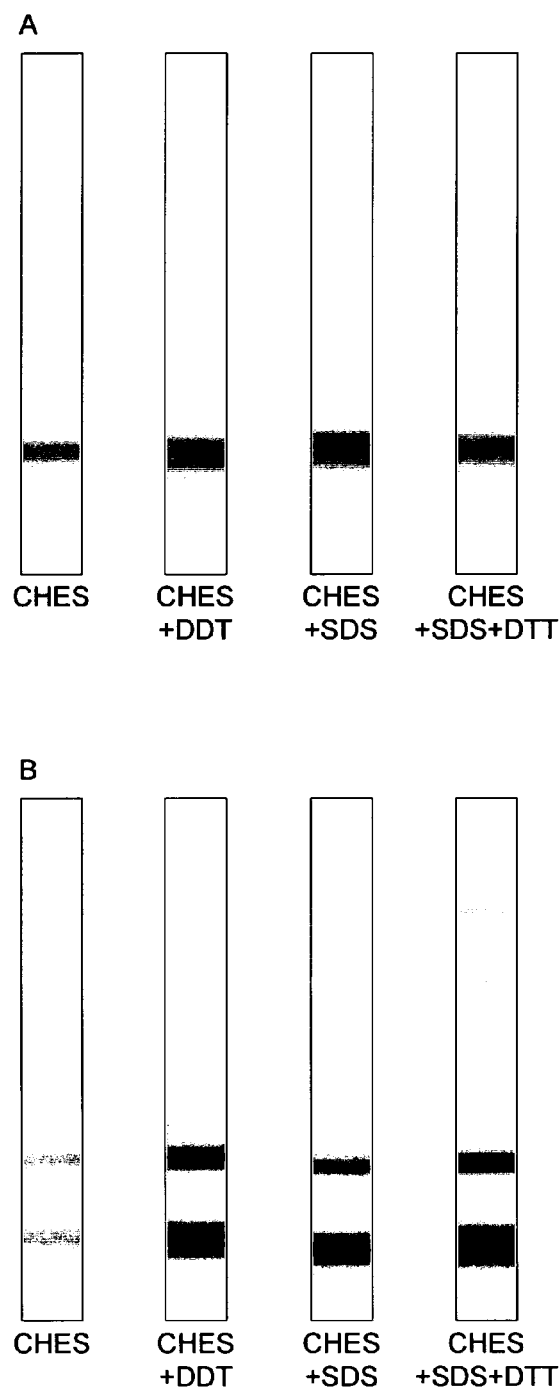
FIG. 11 shows effect of incubating Py-4 with CHES buffer at different temperatures.

FIG. 11 illustrates the effect of incubating Py-4 with CHES buffer at different temperatures. In part A, data shows that sample incubation with Py-4 in CHES buffer, even with additives, does not lead to sample labelling at room temperature. In part B, by increasing the incubation temperature to 95° C. for 5 minutes, labelling is achieved, although SDS with DTT is required.

Figure 24:
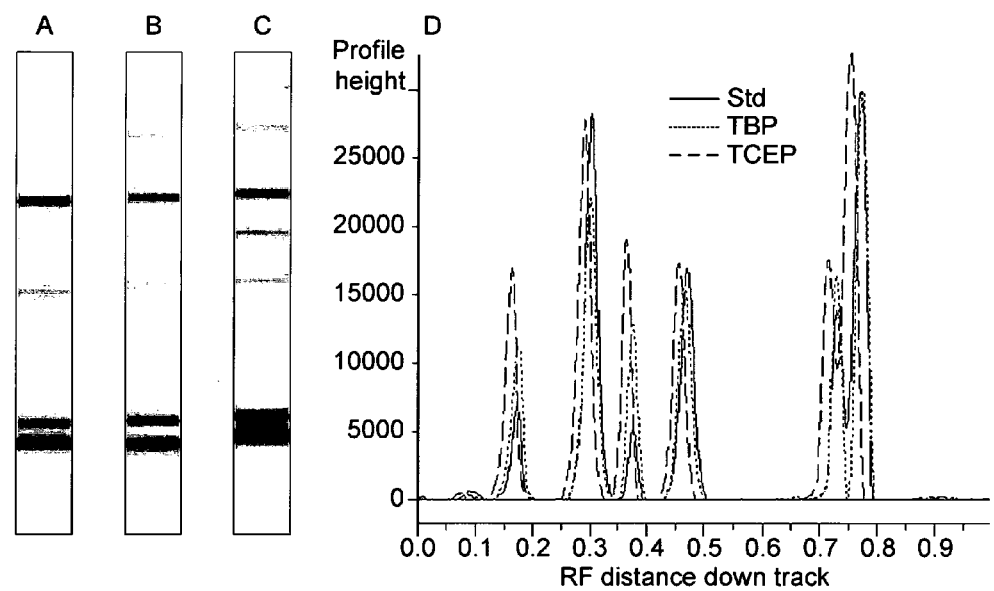
FIG. 24 shows effect of substituting SDS and DTT in the pre stain reaction with alternative denaturing agents.

FIG. 24 demonstrates the effect of substituting SDS and DTT in the pre stain reaction with alternative denaturing agents. In part A the standard pre stain reaction is shown performed in the presence of CHES buffer for 5 minutes at 95° C. using the Lab901 protocol of Py-6 pre dilution in DMF. In part B, the same reaction but containing Tributyl phosphine (TBP) at 1 mM instead of DTT, while in part C 5 mM tris(2-carboxyethyl)phosphine (TCEP) was used. Part D shows an electropherogram profile of each sample. Both TCEP and TBP in particular gave good labelling across all proteins, with a higher average peak height. TCEP is preferred due to improved peak shape and efficiency of sample denaturation at lower concentrations.

Figure 25:
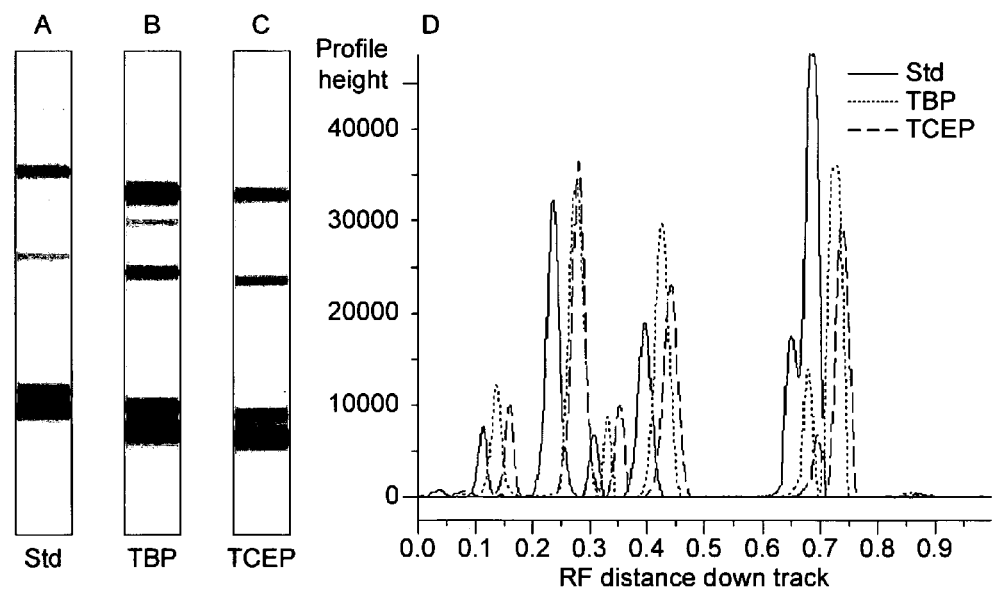
FIG. 25 shows the effect of using different denaturing agents in the sample loading buffer.

FIG. 25 shows the effect of using different denaturing agents in the sample loading buffer. In part A, the standard loading buffer containing mercaptoethanol was used, while in part B 5 mM TBP was used, and in part C 5 mM TCEP used. All samples were denatured for 5 minutes at 95° C. An electropherogram profile in part D shows that TBP increases average sample peak height, however all reagents are suitable in the loading buffer. Ranges of both TBP and TCEP were tested between 5 and 20 mM. TCEP is preferred due to improved peak shape and efficiency of sample denaturation at lower concentrations.

EXAMPLE 2

The experiments that make up this example were conducted to illustrate the effects of the modified protocol compared to the manufacturer's protocol.

Experiment 6

Figure 9:
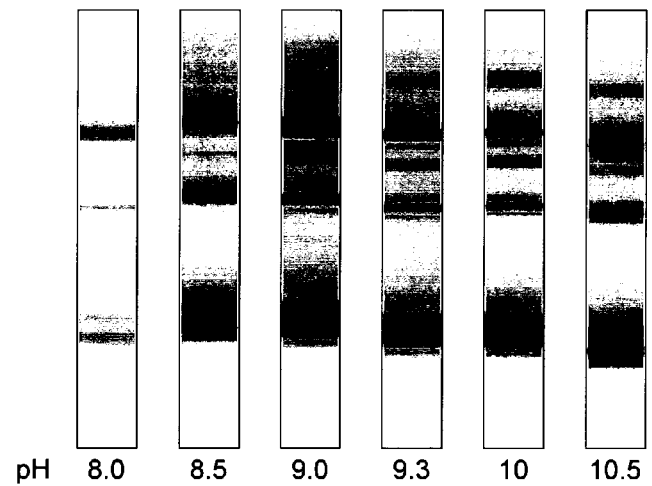
FIG. 9 shows results using the modified protocol at 95° C. and 5 minute incubation in the presence of CAPSO buffer at different pH values.

FIG. 9 shows results using the modified protocol; 95° C. and 5 minute incubation in the presence of CAPSO buffer at different pH values. Py-6 was added from a diluted stock. Best staining of the protein ladder was achieved at between pH9-pH 10 (preferably between 9.3 and 10). Below this level and staining is less efficient, and at pH10.5 band resolution is reduced (bands are broader).

Figure 10:
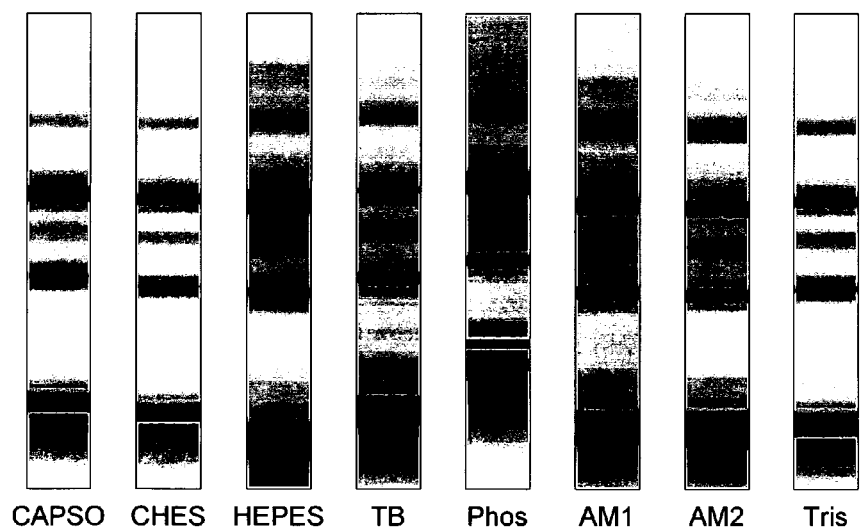
FIG. 10 shows the effect of different buffer reagents on sample pre-staining with Py-6.

FIG. 10 shows the effect of different buffer reagents on sample pre staining with Py-6. The modified protocol was used here, in the presence of additives for 5 minutes at 95° C. HEPES and phosphate buffers are not preferred, as bands are broad and staining is poor. Good staining was achieved with all other buffers.

Figure 12:
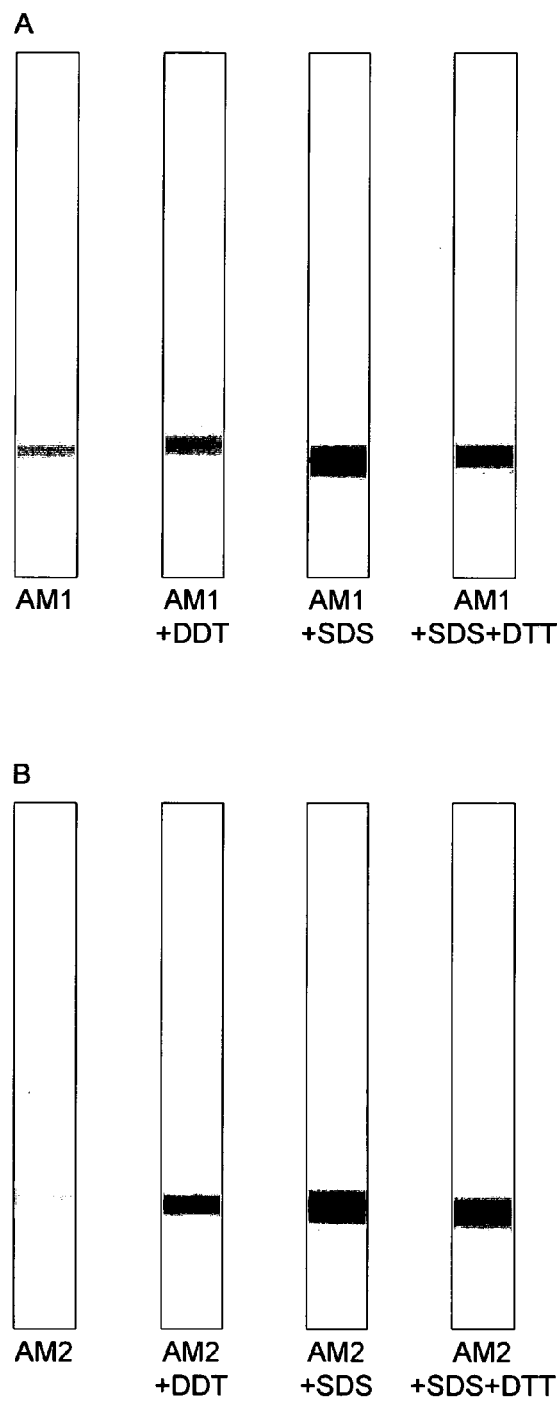
FIG. 12 shows the effect of temperature on Py-4 pre-staining with the manufacturer's AM1 buffer.

FIG. 12 shows the effect of temperature on Py-4 pre staining with the manufacturer's AM1 buffer. In part A, at room temperature, no staining is visible. In part B, increasing incubation time to 60 minutes at 50° C. does not lead to labelling.

Figure 26:
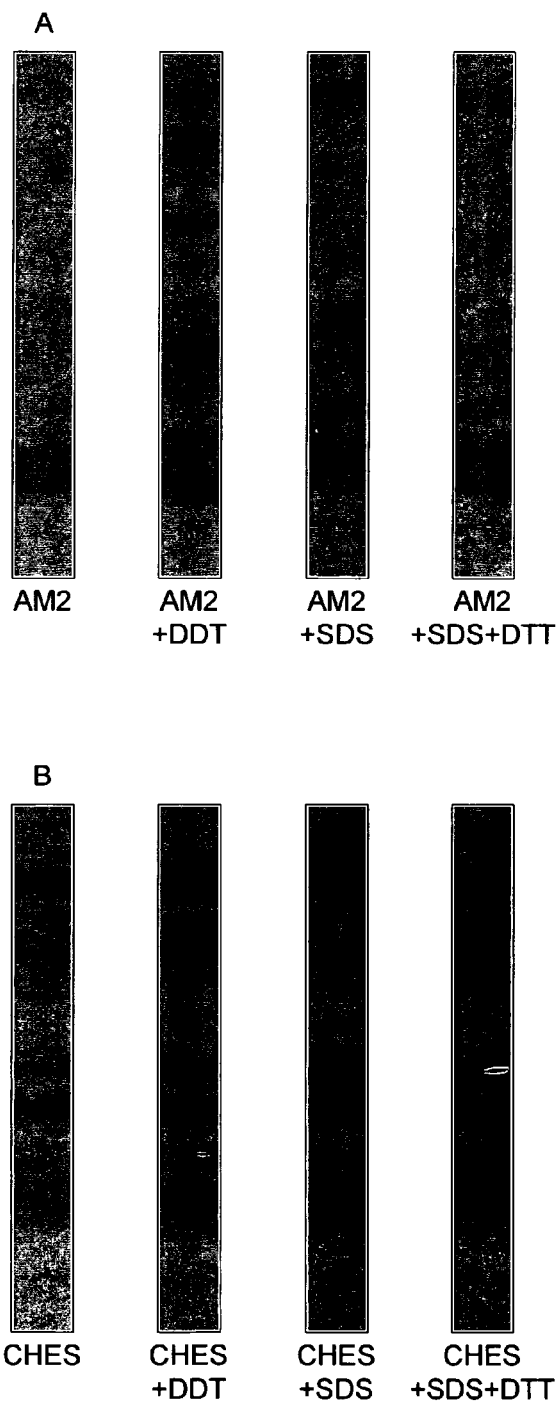
FIG. 26 shows data obtained with Py-8 with CHES buffer and manufacturers AM2 buffer solution.

FIG. 26 shows data obtained with Py-8, with CHES buffer and manufacturers AM2 buffer solution. In part A, sample ladder was incubated with AM2 buffer at 50° C. for 60 minutes. In part B, CHES buffer was used at 95° C. for 5 minutes. Staining with CHES buffer in the presence of additives revealed all ladder proteins. No staining was achieved with AM1 buffer for 30 minutes at room temperature (data not shown), even at 500 µM final concentration of Py-8, furthermore staining with Py-8 using AM2 buffer was not improved at this higher concentration also.

Figure 27:
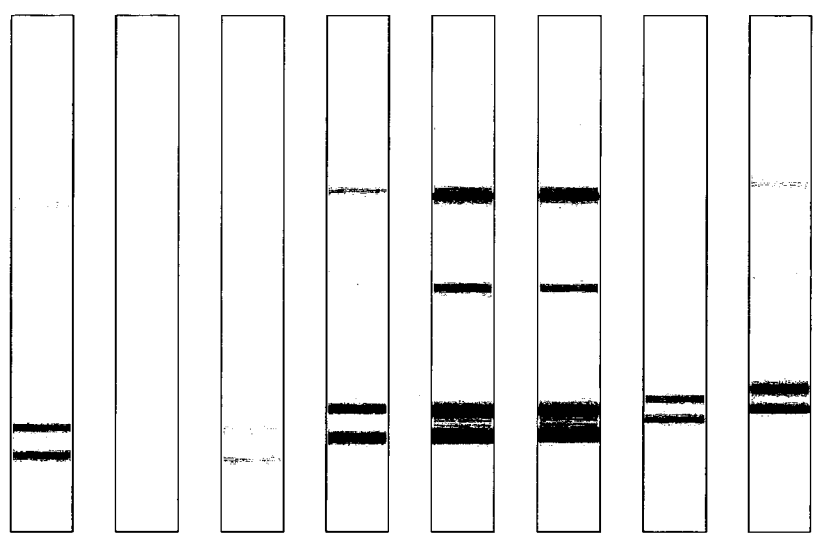
FIG. 27 shows the effect of temperature on protein pre-staining with Py6 using the Lab901 protocol with CHES buffer in the presence of additives.

FIG. 27 shows the effect of temperature on protein pre-staining with Py6 using the Lab901 protocol, with CHES buffer in the presence of additives. Samples were incubated for 5 minutes at the temperature indicated.

EXAMPLE 3

The experiments that make up this example were conducted to demonstrate the applicability of the protocol of the invention to conventional slab gel electrophoresis methods.
Experiment 7

Figure 20:
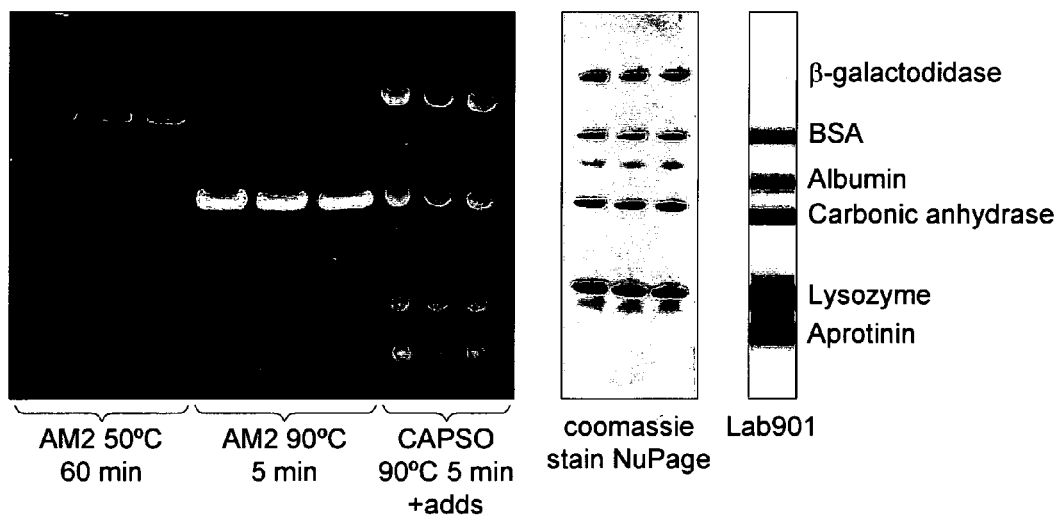
FIG. 20 shows data obtained with Py-6, pre staining a protein ladder prior to analysis on a pre cast slab gel.

FIG. 20 shows data obtained with Py-6, pre staining a protein ladder prior to analysis on a pre cast slab gel. The manufacturer's protocol was followed, incubating with AM2 buffer for 60 minutes at 50° C., or with AM2 buffer for 5 minutes at 95° C. In addition, Py-6 was tested at reduced concentration as described in Example 5 above (diluted Py-6 sample), with CAPSO buffer in the presence of SDS and DTT at 95° C. for 5 minutes. A sample of the same protein separated on an identical gel is shown stained with colloidal coomassie blue. An image obtained following sample pre staining and analysis on ScreenTape is also shown for comparison.

Figure 21:
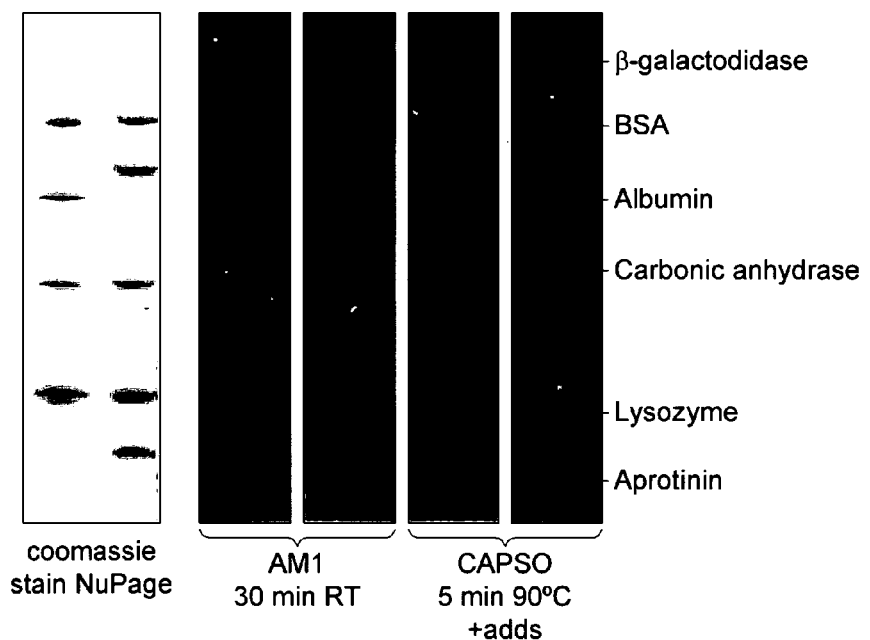
FIG. 21 shows data obtained with Py-1 with samples analysed on a pre cast slab gel.

FIG. 21 shows data obtained with Py-1, with samples analysed on a pre cast slab gel. The manufacturer's protocol and modified protocol are compared, with CAPSO buffer in the presence of SDS and DTT, incubated at 95° C. for 5 minutes, giving better performance. A colloidal coomassie stained ladder is shown for comparison.

Figure 22:
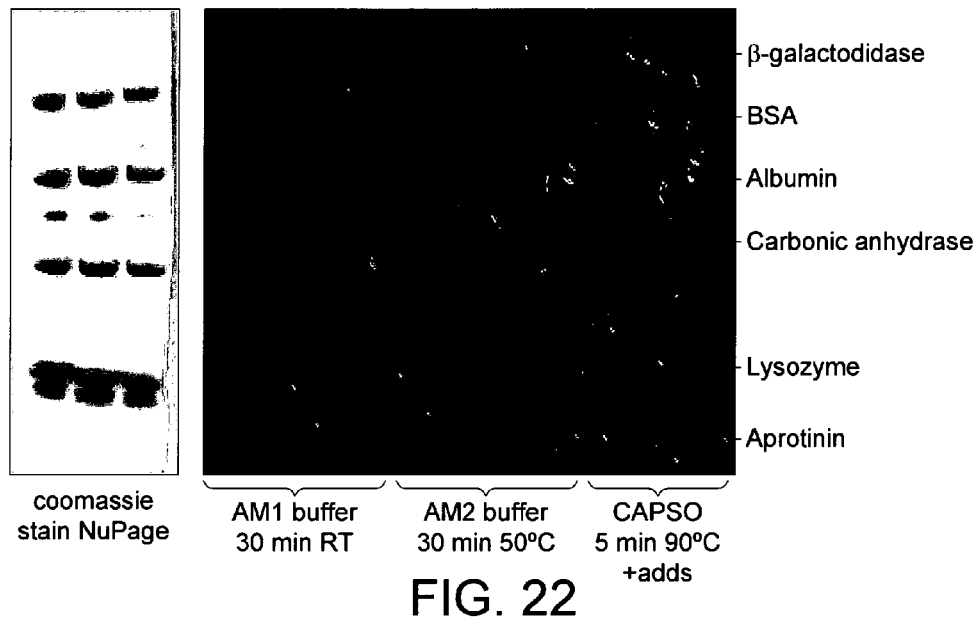
FIG. 22 shows data obtained with Py-4 analysed on a pre cast slab gel.

FIG. 22 shows data obtained with Py-4, analysed on a pre cast slab gel. Using both manufacturer's protocols for AM1 and AM2 buffers, best results were obtained with the modified protocol, using CAPSO buffer, with SDS and DTT for 5 minutes at 95° C.

Figure 23:
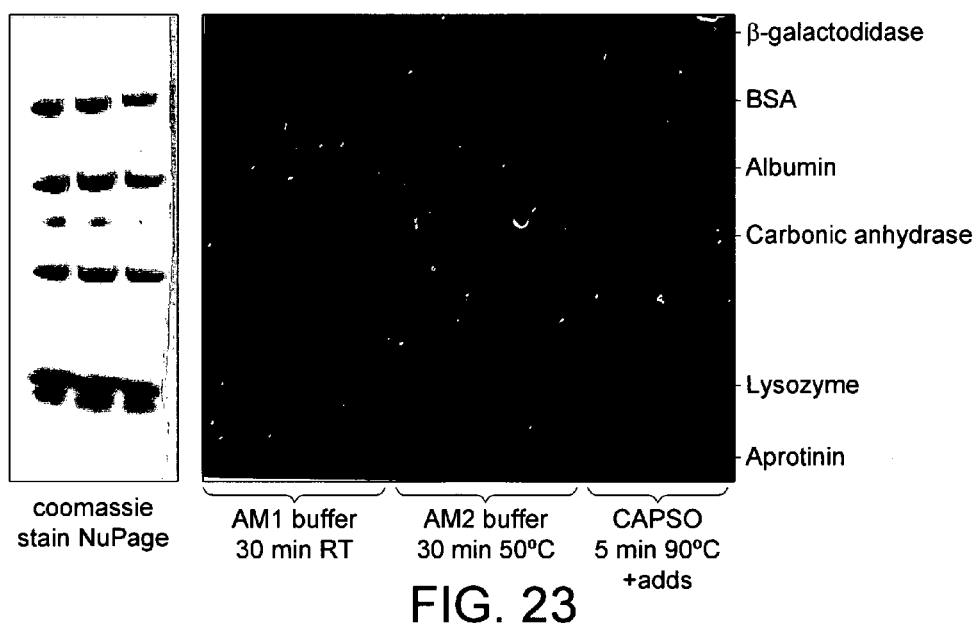
FIG. 23 shows data obtained with Py-2 analysed on a pre cast slab gel.

FIG. 23 shows data obtained with Py-2, analysed on a pre cast slab gel. Using both manufacturer's protocols for AM1 and AM2 buffers, best results were obtained with the modified protocol, using CAPSO buffer, with SDS and DTT for 5 minutes at 95° C., with all six bands in the protein ladder detected.

EXAMPLE 4

This series of experiments was conducted to demonstrate the effects of varying pH and buffer.

Experiment 8

Figure 14:
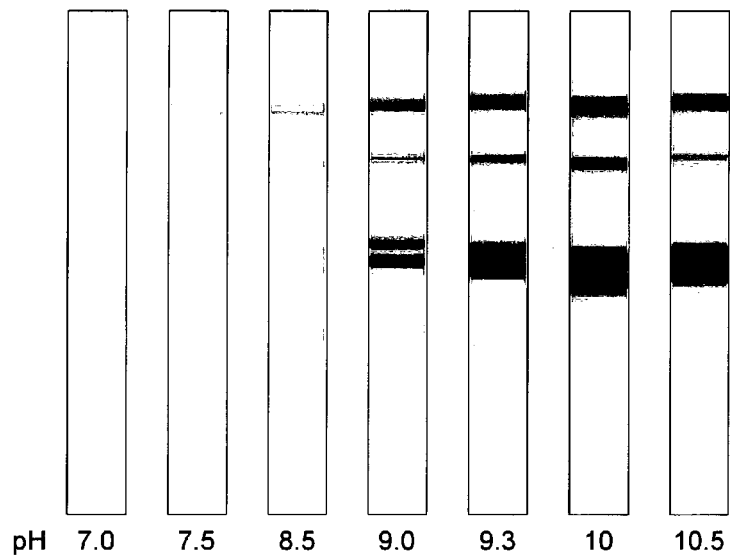
FIG. 14 shows effect of pH upon staining efficiency with Py-4.

FIG. 14 demonstrates the effect of pH upon staining efficiency with Py-4. Using CAPSO buffer at pH values from pH7 to pH10.5, labelling was best between pH9.0 and pH10, with best linearity obtained at pH9.3. Below pH9.0 labelling is faint, while at pH10.5 protein bands are broad and resolution compromised.
Experiment 9

Figure 15:
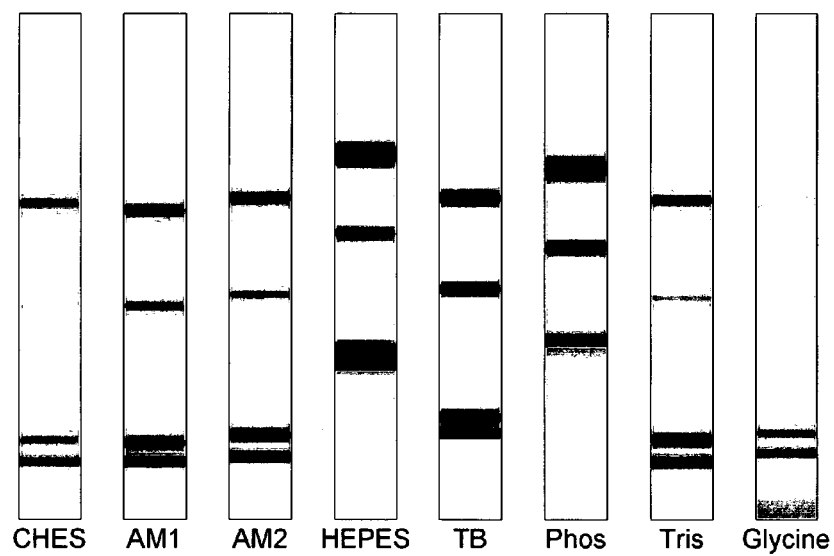
FIG. 15 shows effect of different buffers on protein sample labelling with Py-4 following the Lab901 protocol in the presence of additives at 95° C. for 5 minutes.

FIG. 15 shows the effect of different buffers on protein sample labelling with Py-4 following the Lab901 protocol in the presence of additives at 95° C. for 5 minutes. The staining was poor with HEPES, and phosphate buffers. Tetraborate was not favourable also.
Experiment 10

Figure 17:
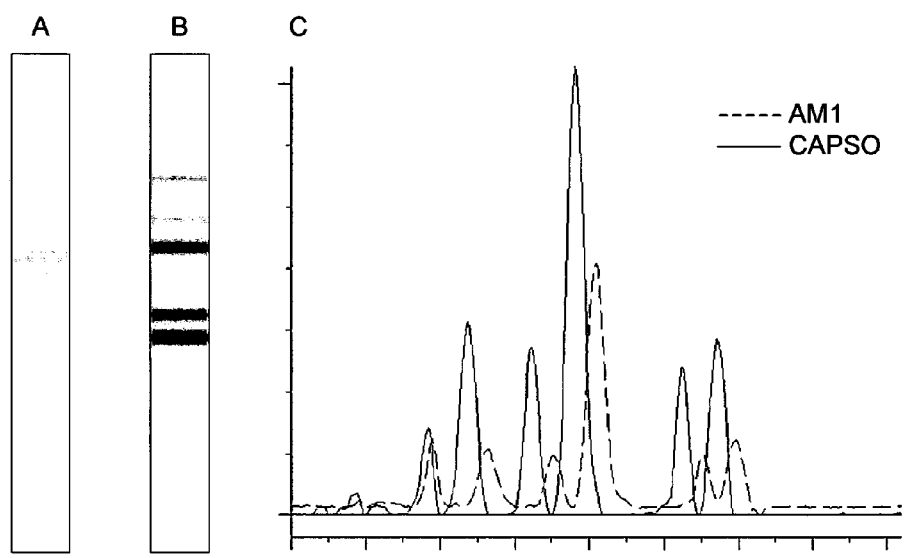
FIG. 17 shows the effect of buffer choice on pre-staining a protein ladder with Py-1 at 95° C. for 5 minutes.

FIG. 17 shows the effect of buffer choice on pre-staining a protein ladder with Py-1 at 95° C. for 5 minutes. In part A, AM1 was used, whereas in part B CAPSO pH9.3 was used. Better staining intensity was achieved with CAPSO buffer.
Experiment 11

Figure 18:
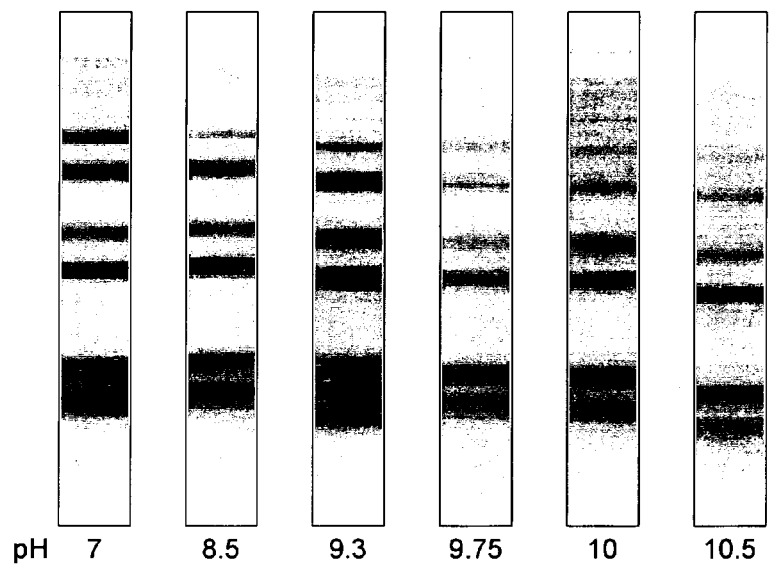
FIG. 18 shows the effect of pH on protein sample staining with Py-1.

FIG. 18 shows the effect of pH on protein sample staining with Py-1. Using CAPSO buffer between pH7.0 and 10.5, best staining was achieved at pH9.3. Above this pH and staining is weak.
Experiment 12

Figure 19:
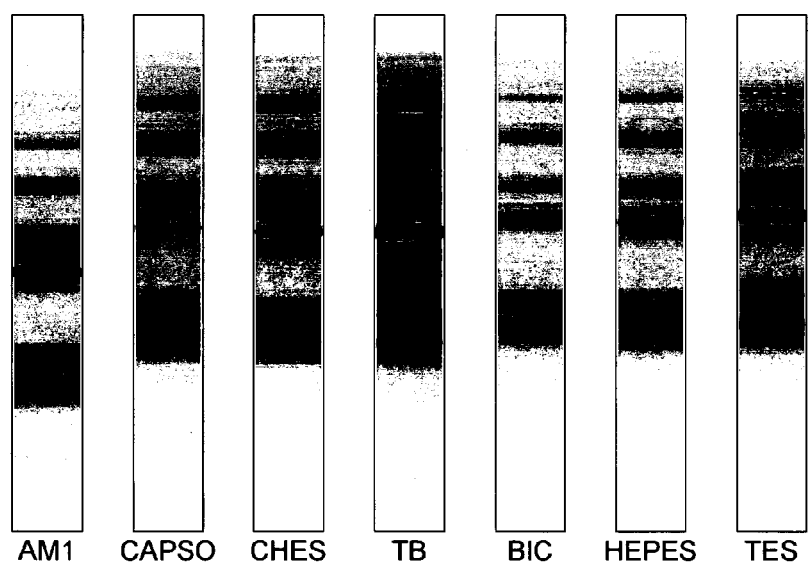
FIG. 19 shows the effect of different buffers on staining efficiency with Py-1.

FIG. 19 shows the effect of different buffers on staining efficiency with Py-1, using the Lab901 protocol. Sodium bicarbonate (pH9.3) was poor and HEPES pH9.3 not favourable also. TES and tetraborate gave good, equal labelling across all proteins in the ladder sample.
Experiment 13

Figure 4:
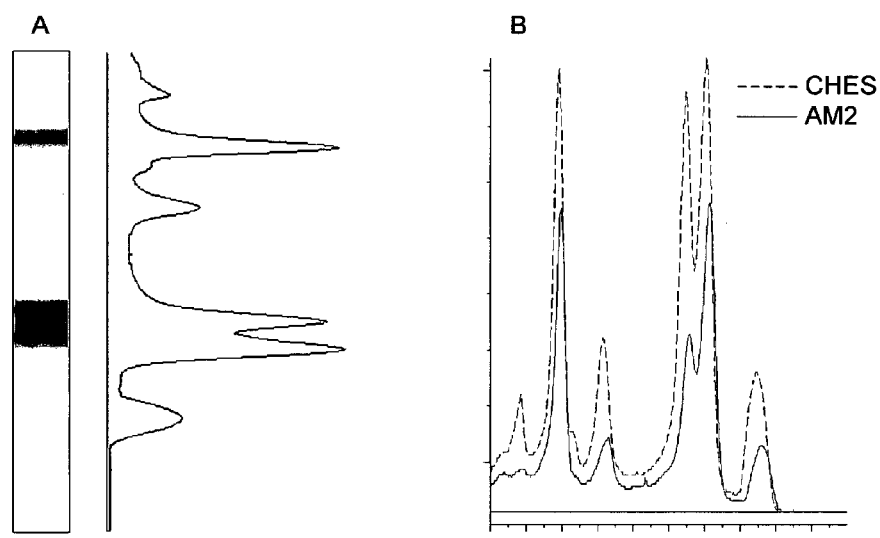
FIG. 4 shows effect of labelling proteins with Py-6 in the presence of CHES buffer.

FIG. 4 shows the effect of labelling proteins with Py-6 in the presence of CHES buffer. Part A is an incubation at 50° C. incubations for 60 minutes, and show improved staining of higher molecular weight proteins as well as good labelling of small proteins. Part B shows an electropherogram comparing profiles from the manufacturer's protocol using AM2 buffer, from FIG. 1A with CHES buffer (FIG. 4A), both for 60 minutes at 50° C.

EXAMPLE 5

The experiments that make up this example demonstrate the effects of varying temperature.

Figure 2:
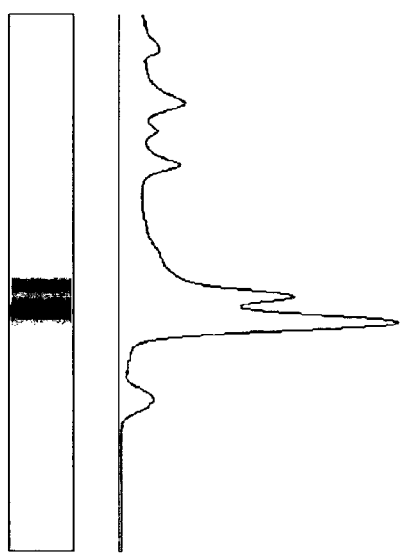
FIG. 2 shows effect of increasing incubation temperature to 95° C. for only 5 minutes using AM2 buffer with Py-6.

FIG. 2 shows the effect of increasing incubation temperature to 95° C., for only 5 minutes, using AM2 buffer with Py-6. The result reveals improved labelling of lower molecular weight proteins, however other proteins are still poorly stained.

Figure 3:
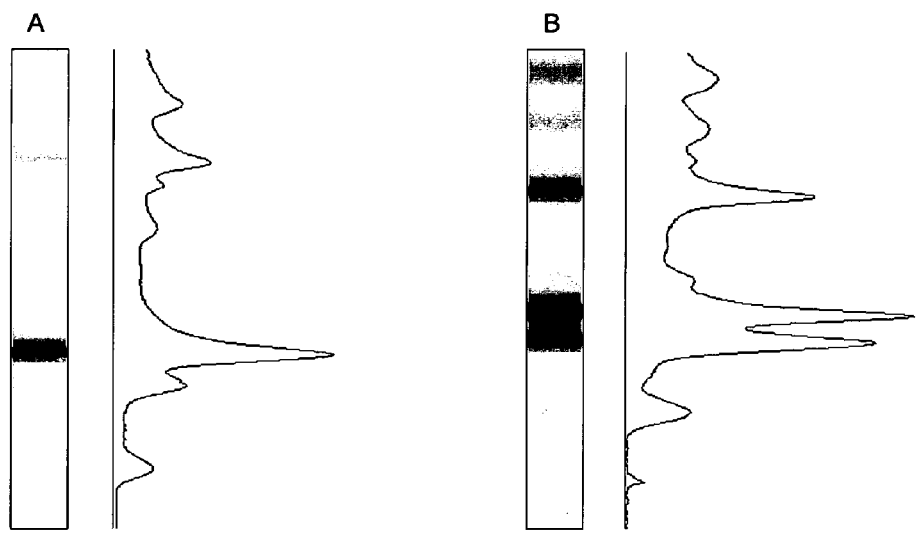
FIG. 3 shows effect of temperature on pre staining a protein ladder with Py-6 in the presence of 5 mM sodium tetraborate buffer.

FIG. 3 shows the effect of temperature on pre staining a protein ladder with Py-6 in the presence of 5 mM sodium tetraborate buffer (as used in Craig et al., Electrophoresis). In part A samples were incubated for 60 minutes at 50° C., whereas in part B, samples were incubated for 5 minutes at 95° C. Improved staining of lower molecular weight species can be seen at a higher temperature, as well as slightly better labelling of some higher molecular weight proteins.

Figure 5:
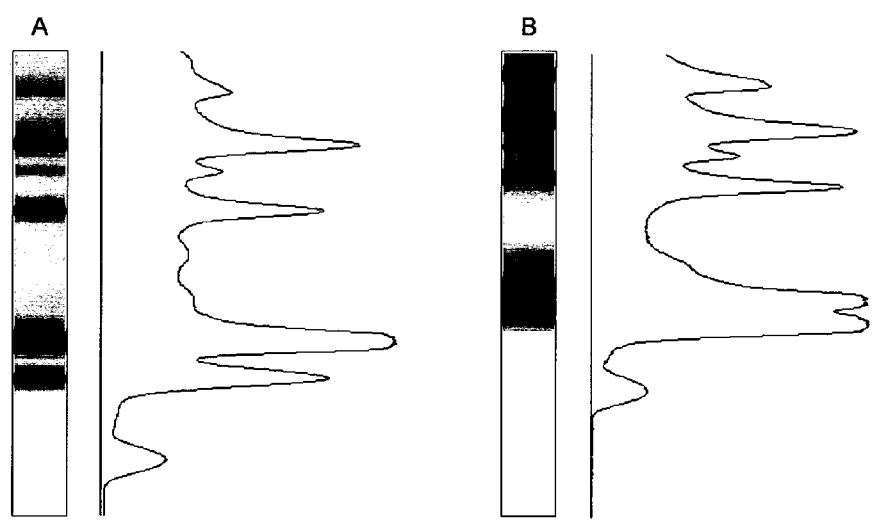
FIG. 5 shows effect of temperature on sample pre staining with Py-6 in the presence of CHES buffer for 5 minutes at 95° C.

FIG. 5 shows the effect of temperature on sample pre staining with Py-6 in the presence of CHES buffer for 5 minutes at 95° C. More intense sample labelling is observed of all ladder proteins, with all 6 now visible. This is an improvement with temperature, incubation time and buffer.

A fluorimetry time course experiment was carried out to further demonstrate the optimum staining temperature and time for protein samples. Experiments were carried out using a fluorimeter (BMG Labtech Fluostar Omega). Samples of prestain solution containing a final concentration of 0.25 mg/ml BSA were added to the plate. Duplicate 65° C., 75° C., 85° C., and 95° C. 4, 6, 8, 10 and 12 minute time course incubations were carried out and analysed alongside a set of negative controls (0 minute incubations) in triplicate from an average reading taken from 30 exposure cycles.

Figure 28:
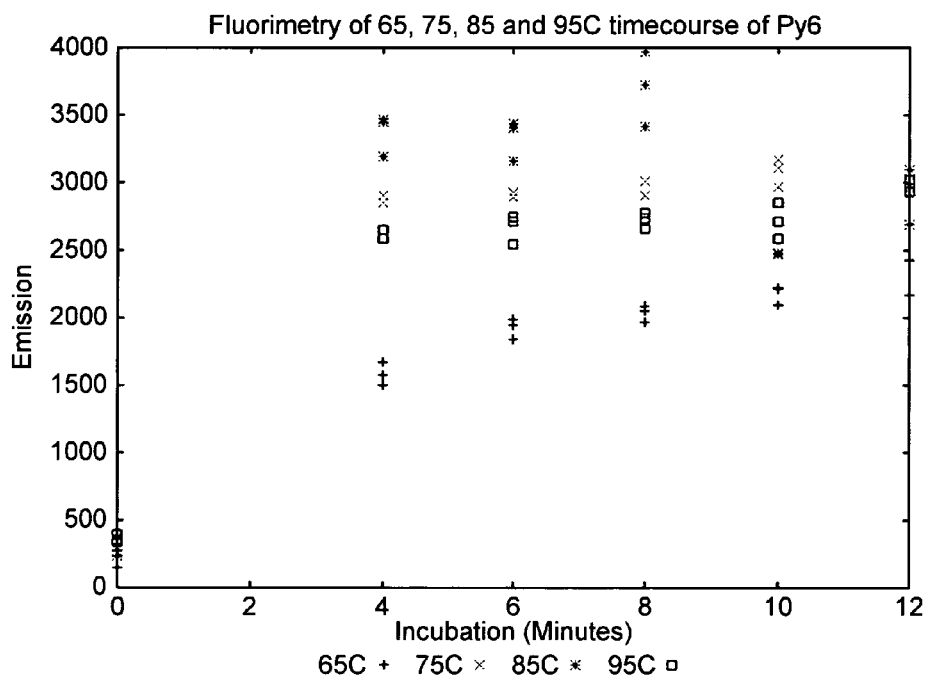
FIG. 28 shows results of a time course analysis of Py6 staining BSA using fluorimetry.

Data presented in FIG. 28 demonstrates the results of a time course analysis of Py6 staining BSA using fluorimetry. The results show that while incubations of a protein sample with Py6 at 85° C. give highest intensity peaks, the variation in sample fluorescence at between 4 and 12 minutes is considerable. The reproducibility of staining is improved by staining at 75° C., where the sample intensity is comparable between 4 and 12 minutes.

At 65° C. the reaction does not reach completion within 12 minutes; however the data is consistent with that produced during initial feasibility testing and thus lend some credence to the results produced at other temperatures.

At 75° C. a higher more stable signal is produced than at 65° C., with % CV values from the 4-12 minute region within 4%.

At 85° C. the quantum yield obtained is higher than that at either 65° C. or 75° C., however the % CV of the readings in the 4-12 minute window is almost always >4%.

While at 95° C., the overall response is reduced to a level below that seen at 75° C., the reproducibility of that is comparable to that seen at 75° C.

Overall, the data indicate that in balancing response against reproducibility 75° C. gives the largest incubation window which maintains a reproducible signal.

A 7 minute incubation at 75° C. for 7 minutes is preferred, as this lies within a window of robustness as regards temperature and timing of incubations.

The invention claimed is:

1. A method for pre-staining a protein sample prior to electrophoresis, comprising reacting the protein sample with a pyrylium dye in the presence of a buffer, a detergent and a denaturing agent to produce a labeled protein sample.

2. The method according to claim 1 wherein the dye has a low quantum yield when unconjugated and a high quantum yield when conjugated.

3. The method according to claim 1, wherein the pyrylium dye is a non-sterically hindered pyrylium dye.

4. The method according to claim 2, wherein the detergent comprises SDS.

5. The method according to claim 1, wherein the denaturing agent comprises one or more of DTT, tributyl-phosphine (TBP) and tris(2-carboxyethyl)phosphine (TCEP).

6. The method according to claim 1, wherein incubation is carried out at a pH from 9 to 10.

7. The method according to claim 5, wherein the incubation is carried out at about pH 9.3.

8. The method according to claim 1, wherein incubation is carried out at a temperature of from 70 to 95° C. and for from 1 to 60 minutes.

9. The method according to claim 8, wherein incubation is carried out at about 75° C. for about 7 minutes.

10. The method according to claim 1, wherein the buffer includes a sulphonate group.

11. The method according to claim 10, wherein the buffer comprises one or more of CAPSO, CHES, TAPS, TES and HEPES.

12. A gel-electrophoresis method, the method comprising the steps of pre-staining a protein sample using a protocol according to claim 1 and electrophoresing the sample on a gel.

13. The method according to claim 12, wherein the gel is a cross-linked polyacrylamide gel.

14. A kit for performing a protein pre-stain protocol, the kit comprising a mixture comprising a pyrylium dye, a detergent and a denaturing agent.

15. The kit according to claim 14, wherein the detergent comprises SDS.

16. The kit according to claim 14, wherein the denaturing agent comprises one or more of DTT, tributyl-phosphine (TBP) and tris(2-carboxyethyl)phosphine (TCEP).

17. The kit according to claim 14, further comprising a buffer that includes a sulphonate group.

18. The kit according to claim 17, wherein the buffer comprises one or more of CAPSO, CHES, TAPS, TES and HEPES.

19. The kit according to claim 14, further comprising an electrophoresis vessel, the vessel including a prepackaged electrophoresis gel.

20. The kit according to claim 19, the electrophoresis vessel being an integrally formed plastics strip or continuous tape, having one or a plurality of electrophoresis volumes formed therein, each volume including a prepackaged electrophoresis gel.

* * * * *

UNITED STATES PATENT AND TRADEMARK OFFICE
CERTIFICATE OF CORRECTION

PATENT NO.      : 8,303,790 B2
APPLICATION NO. : 12/678097
DATED           : November 6, 2012
INVENTOR(S)     : Helen McNeill et al.

It is certified that error appears in the above-identified patent and that said Letters Patent is hereby corrected as shown below:

In column 11, line 38, in Claim 2, delete "1" and insert -- 1, --, therefor.

In column 12, line 19, in Claim 12, delete "1" and insert -- 1, --, therefor.

Signed and Sealed this
First Day of January, 2013

David J. Kappos
*Director of the United States Patent and Trademark Office*